United States Patent [19]

Guggenheim et al.

[11] Patent Number: 4,814,496

[45] Date of Patent: Mar. 21, 1989

[54] SPIRO(BIS)INDANE BIS(CARBOXYPHENYL ETHERS) AND DERIVATIVES THEREOF

[75] Inventors: Thomas L. Guggenheim, Scotia; Sharon J. McCormick, Schenectady, both of N.Y.

[73] Assignee: General Electric Company, Schenectady, N.Y.

[21] Appl. No.: 157,009

[22] Filed: Feb. 18, 1988

[51] Int. Cl.$^4$ ................. C07C 62/06; C07C 69/76
[52] U.S. Cl. ..................... 562/466; 560/56; 260/544 B
[58] Field of Search ............ 560/56; 562/466; 260/544 B

[56] References Cited

U.S. PATENT DOCUMENTS 4,734,482 3/1988 Tamai et al. .................. 528/185

FOREIGN PATENT DOCUMENTS 192480 8/1986 European Pat. Off. .
62-50375 3/1987 Japan .
62-108849 5/1987 Japan .

Primary Examiner—Paul J. Killos
Attorney, Agent, or Firm—William H. Pittman; James C. Davis, Jr.; James Magee, Jr.

[57] ABSTRACT

Esters of spiro(bis)indane bis(carboxyphenyl ethers) are prepared by the reaction of spiro(bis)indane bisphenol di-(alkali metal) salts with nitro- or chloro-substituted benzoic acid esters, and may be converted to the free acids and thence to the acid chlorides. The latter are useful for preparation of macrocyclic polyamide oligomers.

6 Claims, No Drawings

SPIRO(BIS)INDANE BIS(CARBOXYPHENYL ETHERS) AND DERIVATIVES THEREOF

This invention relates to the chemistry of spiro(bis)indanes, and more particularly to intermediates useful in the preparation of macrocyclic spiro(bis)indane polyamide oligomers.

It has recently been discovered that compounds containing spiro(bis)indane moieties undergo particularly facile conversion to macrocyclic oligomers of various types. Reference is made, for example, to copending, commonly owned application Ser. No. 146,154, filed Jan. 20, 1988, which discloses a wide variety of macrocyclic oligomers derived from 6,6'-disubstituted 3,3,3',3'-tetramethylspiro(bis)indanes, especially those which are otherwise unsubstituted and which are hereinafter sometimes simply designated "spirobiindanes". Also of interest is application Ser. No. 20,264, filed Feb. 27, 1987, which discloses spirobiindane bis-aminophenoxy ethers and their conversion to macrocyclic spirobiindane polyamide oligomers. The latter are in turn convertible to linear copolyamides by reaction with lactams in the presence of basic catalysts.

A new class of spiro(bis)indane derivatives has now been discovered. This class of compounds is characterized by the presence of carboxy groups or functional derivatives thereof, and may be converted to macrocyclic oligomers by reaction with a wide variety of diamines.

In one of its aspects, the invention includes compounds selected from the group consisting of spiro(bis)indane bis(carboxyphenyl ethers) of the formula

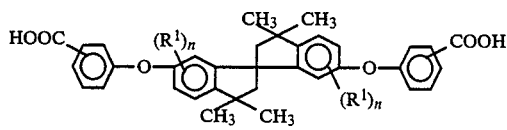

and functional derivatives thereof, wherein each $R^1$ is independently $C_{1-4}$ primary or secondary alkyl or halo, n is 0-3 and the carboxy groups are in the m- or p-positions.

The spiro(bis)indane bis(carboxyphenyl ethers) of formula I are obviously derived from 6,6'-dihydroxy-3,3,3',3'-tetramethylspiro(bis)indanes, which may be substituted or unsubstituted. The $R^1$ values therein may be alkyl radicals such as methyl, ethyl, 1-propyl or 2-propyl, or halo atoms such as chloro or bromo. Among compounds containing such $R^1$ values, methyl and chloro are preferred; however, the most preferred compound is unsubstituted 6,6'-dihydroxy-3,3,3',3'-tetramethylspiro(bis)indane (hereinafter sometimes "SBI"), in which n is 0.

The invention includes bis(carboxyphenyl ethers) in which the carboxy groups are in the m- and p-positions with respect to the ether linkage. In general, the p-carboxyphenyl compounds are preferred. Also within the scope of the invention are functional derivatives of the bis(carboxyphenyl ethers), including salts, acyl halides, esters, amides and mixed anhydrides with such acids as acetic acid and benzoic acid. The free acids, lower alkyl esters ("lower" denoting up to 7 carbon atoms) and especially acyl halides are preferred.

The ester derivatives of the bis(carboxyphenyl ethers) of this invention may be prepared by the nucleophilic displacement reaction of a di-(alkali metal) salt of the spirobiindane bisphenol with a nuclear nitro- or halo-substituted benzoic acid ester, typically a lower alkyl ester and preferably the methyl or ethyl ester. Suitable compounds include ethyl p-nitrobenzoate, ethyl m-nitrobenzoate, methyl p-chlorobenzoate and methyl m-bromobenzoate. The nitro compounds are frequently preferred. The nucleophilic displacement reaction is typically conducted at a temperature of about 80°-125° C. in a dipolar aprotic solvent such as dimethylformamide, dimethylacetamide, dimethyl sulfoxide or N-methylpyrrolidone.

Upon saponification under conventional conditions of the esters thus prepared, the salts of the bis-carboxyphenyl ethers are obtained. The salts may be converted to the free acids, which may in turn be converted to the acyl halides by reaction with such conventional intermediates as phosphorus trichloride, phosphorus pentachloride or thionyl chloride.

The preparation of the bis(carboxyphenyl ethers) of this invention is illustrated by the following examples.

EXAMPLE 1

Freshly cut sodium metal, 14.26 grams (620 mmol.), was added carefully, with stirring, to 1 liter of anhydrous methanol in a nitrogen atmosphere over 2 hours. To the resulting sodium methoxide solution was added, with stirring, 95 grams (310 mmol.) of SBI. Stirring was continued until the mixture was homogeneous after which the methanol was removed under reduced pressure. The resulting SBI disodium salt was washed with two 500-ml. portions of toluene and vacuum stripped, and was finally dried by heating to 100° C. for 12 hours under vacuum.

A mixture of 3.52 grams (10 mmol.) of the SBI disodium salt, 3.93 grams (20 mmol.) of ethyl p-nitrobenzoate and 50 ml. of dry dimethylformamide was heated at 100° C. in a nitrogen atmosphere until homogeneity was achieved. Chloroform, 200 ml. was added and the mixture was extracted three times with aqueous hydrochloric acid solution and once with aqueous sodium chloride solution. The organic phase was dried over anhydrous magnesium sulfate, filtered and vacuum stripped. The residual oil was diluted with methanol and stirred, whereupon a tan solid precipitated which was collected by filtration, washed with methanol and recrystallized from 100% ethanol. There was obtained 4.93 grams (82% of theoretical) of the desired SBI bis(p-carboxyphenyl ether) ethyl ester, melting at 106-108° C. Its identity was confirmed by infrared, proton nuclear magnetic resonance and mass spectroscopy and elemental analysis.

EXAMPLE 2

A mixture of 67.54 grams (112 mmol.) of the product of Example 1, 25.05 grams (447 mmol.) of potassium hydroxide and 500 ml. of ethylene glycol was heated at 120° C., with stirring, until it became homogeneous. The mixture was then poured into aqueous hydrochloric acid solution and the resulting precipitate was collected by filtration, washed with water and air dried. The product, the desired SBI bis(p-carboxyphenyl ether), was obtained in 99% yield and had a melting point of 318°-321° C. Its identity was confirmed by carbon-13 nuclear magnetic resonance and mass spectroscopy.

EXAMPLE 3

A mixture of 60 grams (110 mmol.) of the SBI bis(p-carboxyphenyl ether) of Example 2 and 750 ml. of thionyl chloride was heated under reflux in a nitrogen atmosphere for 3½ hours, with stirring, whereupon it became homogeneous. The mixture was distilled with the removal of 700 ml. of liquid at atmospheric pressure, and was then diluted with 400 ml. of toluene. Distillation was resumed to remove 350 ml. of liquid, after which toluene addition and distillation were repeated. The residue was cooled and recrystallized from a mixture of hexane and toluene to yield the desired bis(carboxy ether) chloride, melting at 161°–163° C., in 96% yield. Its identity was confirmed by infrared, carbon-13 nuclear magnetic resonance and mass spectroscopy and elemental analysis.

The bis(carboxyphenyl ether) halides of this invention may be converted to macrocyclic polyamide oligomer compositions by reaction with diamines, typically in solution in a substantially inert organic liquid. Any suitable diamine may be employed; examples are m-phenylenediamine, p-phenylenediamine, hexamethylenediamine, 1,3-bis(3-aminopropyl)tetramethyldisiloxane and 1,3-bis(p-aminophenyl)-tetramethyldisiloxane.

Suitable organic liquids include halogenated alkanes such as methylene chloride and chloroform; aprotic polar solvents such as those previously enumerated; aromatic hydrocarbons and chlorinated aromatic hydrocarbons such as toluene, xylene and chlorobenzene; and ethers such as tetrahydrofuran and ethylene glycol dimethyl ether. In most instances, relatively volatile solvents such as methylene chloride, chloroform and tetrahydrofuran are preferred by reason of the ease of removal thereof by evaporation following completion of the reaction.

It is sometimes advantageous to employ a hydrogen chloride acceptor in this reaction. Suitable hydrogen chloride acceptors are moderately strong bases such as alkali metal carbonates and tertiary amines, preferably sodium carbonate, triethylamine and pyridine. The proportion thereof is preferably at least stoichiometric, most often about 1–3 equivalents per calculated equivalent of hydrogen chloride evolved.

Any reaction temperature effective to achieve reaction of the diamine with the bis(carboxyphenyl ether) chloride may be employed. Elevated temperatures, typically in the range of about 35°–100° C., are usually satisfactory, with about 40°–80° C. being preferred.

The macrocyclic polyamide oligomers thus prepared are capable of conversion to linear polyamides, which have uses typical of similar known polyamides.

For example, copolyamides may be prepared of the macrocyclic polyamide oligomers by reaction with at least one lactam in the presence of a basic reagent. Illustrative lactams are pivalolactam, δ-valerolactam, ε-caprolactam and laurolactam, with ε-caprolactam generally being preferred.

Suitable basic reagents include inorganic bases such as the alkali and alkaline earth metals and their hydrides, hydroxides, carbonates and alkoxides, and strong organic bases such as tetraalkylammonium hydroxides, guanidines, and organometallics including Grignard reagents and organolithium reagents. The alkali metal hydrides, especially sodium hydride, are preferred.

The reaction between the lactam, basic reagent and macrocyclic polyamide oligomer composition typically takes place at elevated temperatures. In general, temperatures of about 25°–200° C., preferably about 90°–150° C., are adequate to effect reaction of the lactam with the basic reagent to form an anionic intermediate, which subsequently reacts with the oligomer composition at temperatures in the range of about 20°–300° C. The proportions of lactam and oligomer composition are not critical but may be varied according to the desired stoichiometry of the product.

Macrocyclic polyamide oligomers containing a disiloxane group can be polymerized by the action of a strongly acidic catalyst such as methanesulfonic or trifluoromethanesulfonic acid, a basic catalyst such as an alkali metal phenate, or an alkali metal fluoride. It is also possible to incorporate in the polymerization mixture a cyclic polysiloxane such as cyclooctamethyltetrasiloxane, to increase the molecular weight of the polysiloxane blocks in the linear polyamide product. The resulting polymers and the method for their preparation are disclosed and claimed in copending, commonly owned patent application Ser. No. 182,020 filed 4-15-88.

The proportion of catalyst in the mixture, based on macrocyclic polyimide and cyclic polysiloxane present, may vary widely and is typically about 0.001–10.0 mole percent. Polymerization temperatures are typically in the range of about 125°–200° C. It may sometimes be advantageous to employ a non-polar solvent such as o-dichlorobenzene or 1,2,4-trichlorobenzene as a reaction medium.

The preparation and polymerization of macrocyclic polyamide oligomer compositions is illustrated by the following examples.

EXAMPLE 4

A solution of 7 grams (11.97 mmol.) of SBI bis-(p-carboxyphenyl ether) chloride and 229 ml. of dry, ethanol-free chloroform was heated under reflux in a nitrogen atmosphere, with stirring, and a mixture of 3.78 grams (11.97 mmol.) of 1,3-bis(p-aminophenyl)tetramethyldisiloxane, 1.89 grams (23.92 mmol.) of pyridine and 10 ml. of dry chloroform was added over 1 hour. The mixture was washed twice with aqueous hydrochloric acid solution and once with aqueous sodium chloride solution, dried over magnesium sulfate and filtered. The filtrate was vacuum stripped to yield an off-white solid in 98% yield. Analysis of the solid by high pressure liquid chromatography and field desorption mass spectrometry showed the presence of 94% macrocyclic polyamide oligomers, including the monomeric and dimeric species, and 6% linear polyamide.

EXAMPLE 5

A mixture of 250 mg. of the product of Example 4, 1 gram (3.38 mmol.) of octamethylcyclotetrasiloxane, 5 microliters (0.08 mmol.) of methanesulfonic acid and 2 ml. of dry chloroform was heated at 70° under nitrogen, with stirring, to remove the chloroform. There remained a thick polymeric residue which was shown by gel permeation chromatography to have a weight average molecular weight of about 78,000.

What is claimed is:
1. A compound selected from the group consisting of spiro(bis)indane bis(carboxyphenyl ethers) of the formula

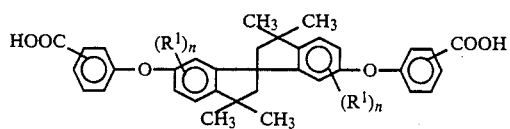

and functional derivatives thereof, wherein each $R^1$ is independently $C_{1-4}$ primary or secondary alkyl or halo, n is 0–3 and the carboxy groups are in the m- or p-positions.

2. A compound according to claim 1 wherein n is 0.

3. A compound according to claim 2 wherein the carboxy groups are in the p-positions.

4. A compound according to claim 3 which is the free carboxylic acid.

5. A compound according to claim 3 which is a lower alkyl ester.

6. A compound according to claim 3 which is the acid chloride.

* * * * *